US011207088B2

(12) United States Patent
Kuriki

(10) Patent No.: US 11,207,088 B2
(45) Date of Patent: Dec. 28, 2021

(54) ENDOSCOPIC SURGICAL DEVICE

(71) Applicant: OLYMPUS CORPORATION, Hachioji (JP)

(72) Inventor: Hiroki Kuriki, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 526 days.

(21) Appl. No.: 16/046,593

(22) Filed: Jul. 26, 2018

(65) Prior Publication Data

US 2018/0325541 A1 Nov. 15, 2018

Related U.S. Application Data

(63) Continuation of application No. PCT/JP2016/053117, filed on Feb. 2, 2016.

(51) Int. Cl.
*A61B 17/29* (2006.01)
*A61B 18/14* (2006.01)
(Continued)

(52) U.S. Cl.
CPC .......... *A61B 17/29* (2013.01); *A61B 18/1445* (2013.01); *A61B 18/1492* (2013.01);
(Continued)

(58) Field of Classification Search
CPC . A61B 17/29; A61B 18/1445; A61B 18/1492; A61B 90/37; A61B 17/3478;
(Continued)

(56) References Cited

U.S. PATENT DOCUMENTS 6,066,102 A  5/2000 Townsend et al.
6,183,469 B1 * 2/2001 Thapliyal .......... A61B 18/1206
604/35
(Continued)

FOREIGN PATENT DOCUMENTS

EP  1726266 A1  11/2006
EP  1752108 A1  2/2007
(Continued)

OTHER PUBLICATIONS

Apr. 5, 2016 International Search Report issued in International Patent Application No. PCT/JP2016/053117.
(Continued)

*Primary Examiner* — Linda C Dvorak
*Assistant Examiner* — Nils A Potter
(74) *Attorney, Agent, or Firm* — Oliff PLC

(57) ABSTRACT

An endoscopic surgical device includes: a sheath; a forceps section protruding from a cover provided at a distal end of the sheath and including a pair of openable-closable forceps components; an operable member that is connected to a proximal end of the forceps section, that opens the forceps components when moved forward in a longitudinal direction, and that closes the forceps components when moved rearward; and a flow-path formation member having a through-hole through which the operable member extends and having a first liquid delivery hole constituted by a gap between the through-hole and the operable member and a second liquid delivery hole constituted by a gap between the flow-path formation member and an inner peripheral surface of the cover. The operable member is provided with a large-diameter section that abuts on the flow-path formation member when the operable member is moved forward to block the first liquid delivery hole.

11 Claims, 7 Drawing Sheets

(51) Int. Cl.
  *A61B 17/34* (2006.01)
  *A61B 18/12* (2006.01)
  *A61B 90/00* (2016.01)
  *A61B 17/00* (2006.01)
  *A61B 18/00* (2006.01)

(52) U.S. Cl.
  CPC ....... *A61B 17/3478* (2013.01); *A61B 18/1206* (2013.01); *A61B 90/37* (2016.02); *A61B 2017/0034* (2013.01); *A61B 2017/00269* (2013.01); *A61B 2017/2929* (2013.01); *A61B 2018/00601* (2013.01); *A61B 2217/007* (2013.01); *A61B 2218/002* (2013.01)

(58) Field of Classification Search
  CPC .... A61B 2017/2929; A61B 2017/0034; A61B 2017/00269; A61B 18/1206; A61B 2018/00601; A61B 2217/007; A61B 2218/002
  USPC .......................................................... 606/41
  See application file for complete search history.

(56) References Cited

U.S. PATENT DOCUMENTS

| | | | |
|---|---|---|---|
| 6,394,964 | B1 | 5/2002 | Sievert, Jr. et al. |
| 2004/0167514 | A1 | 8/2004 | Okada |
| 2004/0210284 | A1 | 10/2004 | Okada |
| 2005/0033278 | A1* | 2/2005 | McClurken ........ A61B 18/1445 606/41 |
| 2005/0228224 | A1* | 10/2005 | Okada ................ A61B 1/00135 600/104 |
| 2006/0270969 | A1 | 11/2006 | Toyonaga et al. |
| 2007/0038213 | A1 | 2/2007 | Machiya et al. |
| 2008/0125809 | A1 | 5/2008 | Suzuki et al. |
| 2011/0282368 | A1* | 11/2011 | Swayze .............. A61B 17/0057 606/159 |
| 2014/0288554 | A1* | 9/2014 | Okada ................ A61B 18/1492 606/45 |
| 2014/0350540 | A1* | 11/2014 | Kitagawa ........... A61B 18/1206 606/34 |
| 2015/0148803 | A1 | 5/2015 | Kaneko et al. |

FOREIGN PATENT DOCUMENTS

| | | |
|---|---|---|
| EP | 1913876 A1 | 4/2008 |
| EP | 1985252 A1 | 10/2008 |
| EP | 1987795 A1 | 11/2008 |
| EP | 2921120 A1 | 9/2015 |
| EP | 2944280 A1 | 11/2015 |
| JP | S61-111402 U | 7/1986 |
| JP | H11-047135 A | 2/1999 |
| JP | 2002-505904 A | 2/2002 |
| JP | 2004-248911 A | 9/2004 |
| JP | 2005-224426 A | 8/2005 |
| JP | 2006-325785 A | 12/2006 |
| JP | 2007-044393 A | 2/2007 |
| JP | 4315725 B2 | 8/2009 |
| JP | 2011-212450 A | 10/2011 |
| JP | 5754557 B2 | 7/2015 |
| WO | 99/45847 A1 | 9/1999 |
| WO | 2007/017949 A1 | 2/2007 |
| WO | 2014/109181 A1 | 7/2014 |

OTHER PUBLICATIONS

Jun. 21, 2016 International Search Report issued in International Patent Application No. PCT/JP2016/053106.
Sep. 20, 2017 Japanese Office Action issued in Patent Application No. 2017-526712.
U.S. Appl. No. 16/046,465, filed Jul. 26, 2018 in the name of Kuriki et al.
Aug. 1, 2019 European Search Report issued in European Patent Application No. 16889247.9.
Apr. 23, 2020 Office Action Issued in U.S. Appl. No. 16/046,465.
Sep. 4, 2020 Office Action issued in U.S. Appl. No. 16/046,465.

* cited by examiner

ENDOSCOPIC SURGICAL DEVICE

CROSS-REFERENCE TO RELATED APPLICATIONS

This is a continuation of International Application PCT/JP2016/053117, with an international filing date of Feb. 2, 2016, which is hereby incorporated by reference herein in its entirety.

TECHNICAL FIELD

The present invention relates to endoscopic surgical devices.

BACKGROUND ART

A known endoscopic surgical device includes forceps that are provided at a distal end of a sheath to be inserted into a channel of an endoscope and that are to be opened and closed by a wire. This endoscopic surgical device delivers water guided via a flow path within the sheath toward a target site from a liquid delivery lumen offset toward the lateral side of the forceps (for example, see Japanese Literature 1).

CITATION LIST

Patent Literature

{PTL 1}
Japanese Unexamined Patent Application, Publication No. 2005-224426

SUMMARY OF INVENTION

An aspect of the present invention provides an endoscopic surgical device including: a sheath insertable into a channel of an endoscope and having a pipe for delivering a liquid; a forceps section that is disposed so as to protrude from a distal end cover provided at a distal end of the sheath and that includes a pair of openable-closable forceps components; an operable member that is connected to a proximal end of the forceps section, opens the forceps components when the operable member is moved forward in a longitudinal direction thereof, and closes the forceps components when the operable member is moved rearward; and a flow-path formation member that has a through-hole through which the operable member extends, the flow-path formation member including a first liquid delivery hole constituted by a gap between the through-hole and the operable member and a second liquid delivery hole constituted by a gap between the flow-path formation member and an inner peripheral surface of the distal end cover. The operable member is provided with a large-diameter section that abuts on the flow-path formation member when the operable member is moved forward so as to block the first liquid delivery hole.

DESCRIPTION OF EMBODIMENTS

An endoscopic surgical device 1 according to an embodiment of the present invention will be described below with reference to the drawings.

Figure 1:
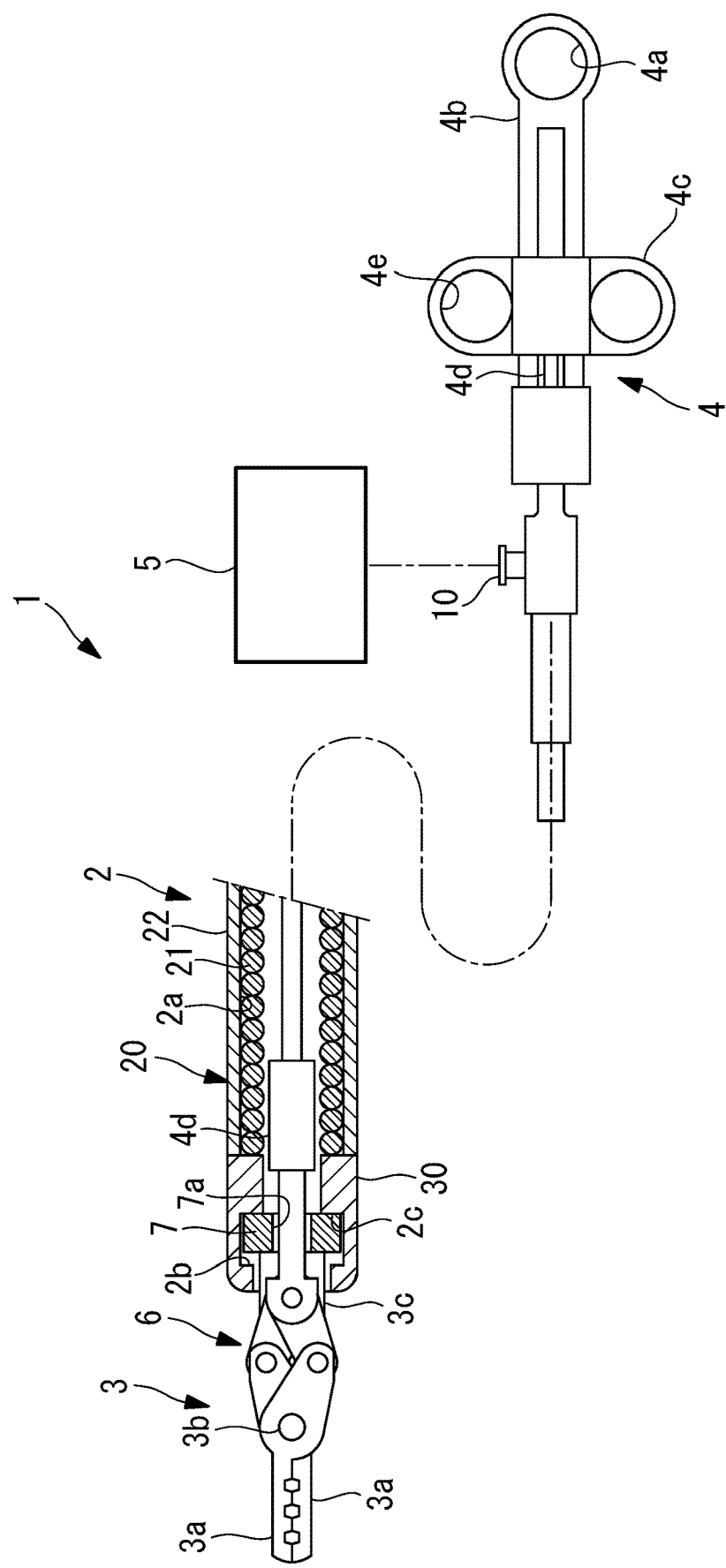
FIG. 1 is an overall configuration diagram in which a distal end section of an endoscopic surgical device according to an embodiment of the present invention is enlarged and in which a part of the endoscopic surgical device is omitted.

For example, the endoscopic surgical device 1 according to this embodiment is a surgical device whose distal end is to be inserted into the body via a channel provided in an insertion section of an endoscope. As shown in FIG. 1, the endoscopic surgical device 1 includes: a flexible sheath 2 having a narrow cylindrical shape insertable into the channel; a forceps section 3 having a pair of forceps components 3a protruding from an opening of a distal end cover 30, to be described later, at the distal end of the sheath 2; an operable section 4 that opens and closes the forceps components 3a by being pushed and pulled at the proximal end of the sheath 2; a wire 4f and an operable member 4d that transmit tension generated by the operable section 4 to the forceps components 3a; and a liquid delivery means 5 that delivers a liquid from the distal end of the distal end cover 30 via a flow path (pipe) 2a constituted by an inner hole of a coil sheath 21.

The sheath 2 includes a sheath body 20 and the distal end cover 30 fixed to the distal end of the sheath body 20. The sheath body 20 includes the coil sheath 21 having an inner diameter larger than the diameter of the operable member 4d, and also includes a cylindrical resin casing 22 that covers the outer surface of the coil sheath 21.

The distal end cover 30 is composed of a rigid material, such as metal, and has an outer diameter that is substantially equal to the outer diameter of the resin casing 22.

The distal end of the distal end cover 30 is provided with a collar section 2b that extends radially inward and that reduces the diameter of the flow path 2a. The inner surface of the distal end cover 30 is provided with a stopper section 2c that protrudes radially inward at a position located away from the collar section 2b toward the proximal end by a predetermined distance.

Figure 2:
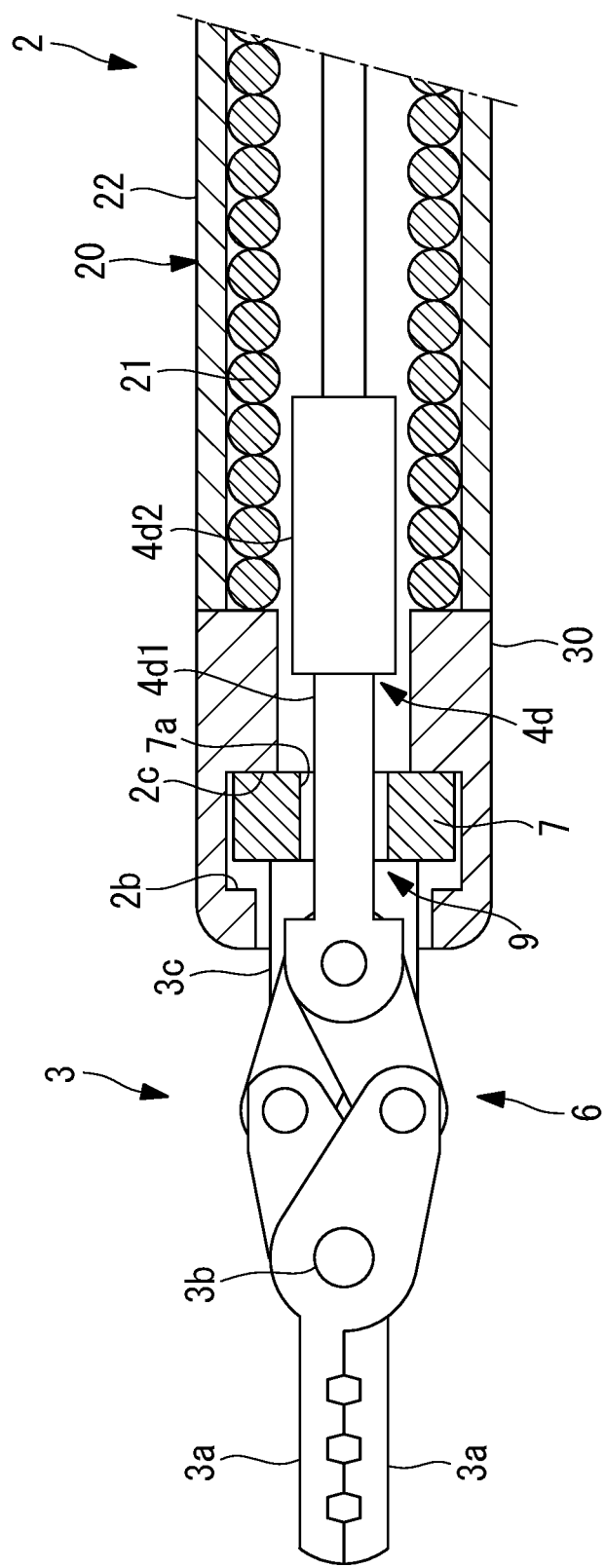
FIG. 2 is an enlarged vertical sectional view illustrating forceps components of the endoscopic surgical device in FIG. 1 in a closed state.
Figure 3:
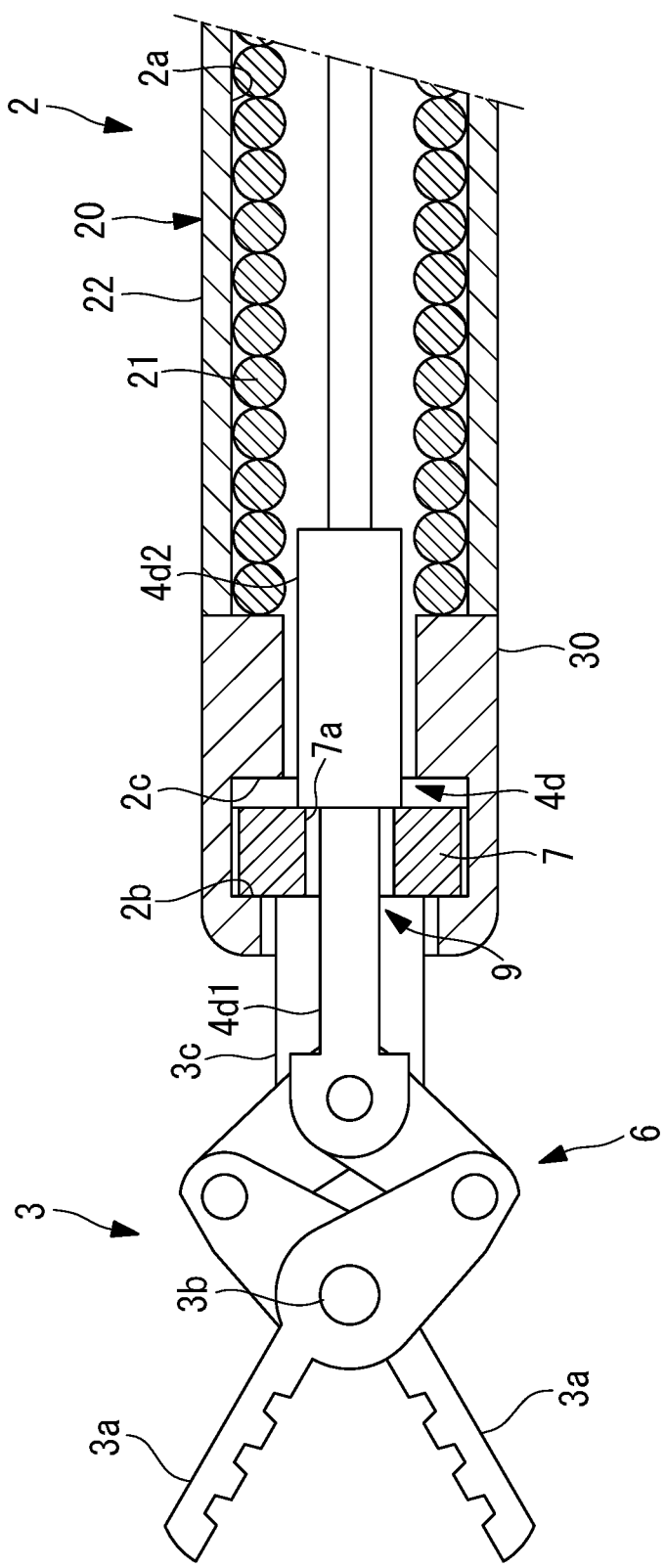
FIG. 3 is an enlarged vertical sectional view illustrating the forceps components of the endoscopic surgical device in FIG. 1 in an open state.

As shown in FIGS. 2 and 3, the forceps section 3 includes a bracket 3c that supports the pair of forceps components 3a in a pivotable manner by means of a pivot shaft 3b. The pair of forceps components 3a are connected to the operable member 4*d* by a link mechanism 6 provided at the proximal ends of the forceps components 3*a*. Thus, when the operable member 4*d* is pulled (retracted) toward the proximal end, the tension of the operable member 4*d* causes the pair of forceps components 3*a* to pivot about the pivot shaft 3*b* in a direction in which the pair of forceps components 3*a* close, as shown in FIG. 2. When the operable member 4*d* is pushed (advanced) toward the distal end, the pair of forceps components 3*a* pivot about the pivot shaft 3*b* in a direction in which the pair of forceps components 3*a* open, as shown in FIG. 3.

The width of the forceps components 3*a* in the opening-closing direction thereof and the width thereof in a direction orthogonal to the opening-closing direction are both set to be smaller than the bracket 3*c*.

Figure 5:
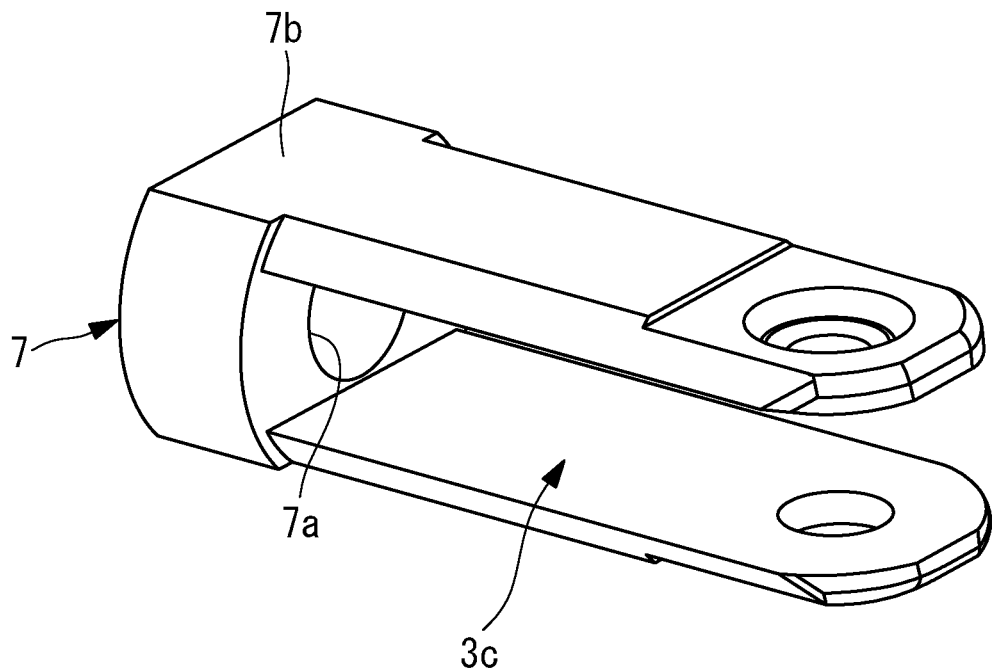
FIG. 5 is a perspective view illustrating a flow-path formation member included in the endoscopic surgical device in FIG. 1.

As shown in FIG. 5, a flow-path formation member 7 having a center hole (through-hole) 7*a* through which the operable member 4*d* can extend is integrally fixed to the proximal end of the bracket 3*c* of the forceps section 3. The flow-path formation member 7 has a shape of a disk with a diameter slightly smaller than the outer diameter of the resin casing 22 and larger than the inner diameter of the collar section 2*b* and includes recesses 7*b* that are recessed at the opposite sides of the center hole 7*a* to radial positions sufficiently smaller than the inner diameter of the collar section 2*b*. The bracket 3*c* and the flow-path formation member 7 may be independent components and may be fixed to each other by, for example, welding or adhering so long as the two components rotate together.

Figure 6:
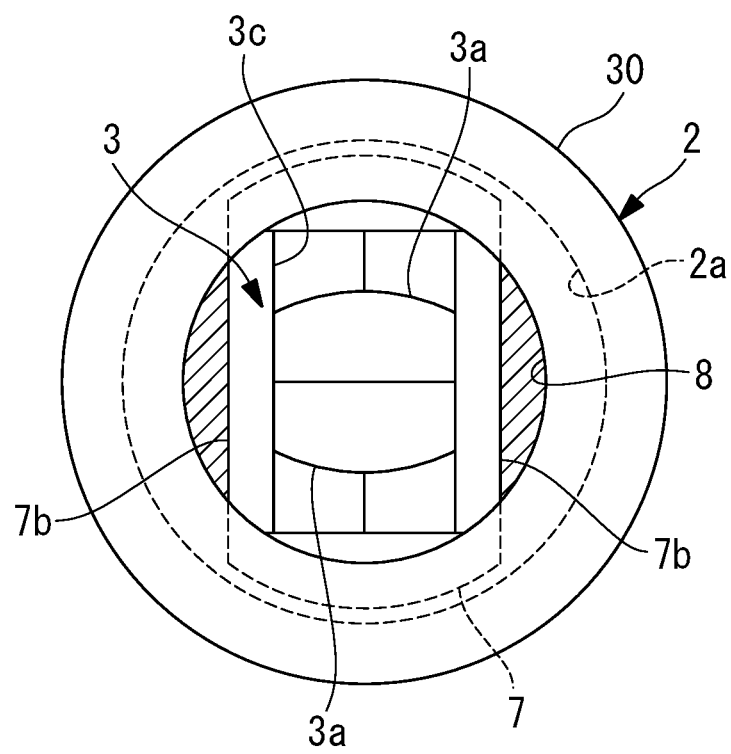
FIG. 6 is a front view of the endoscopic surgical device in FIG. 2.
Figure 7:
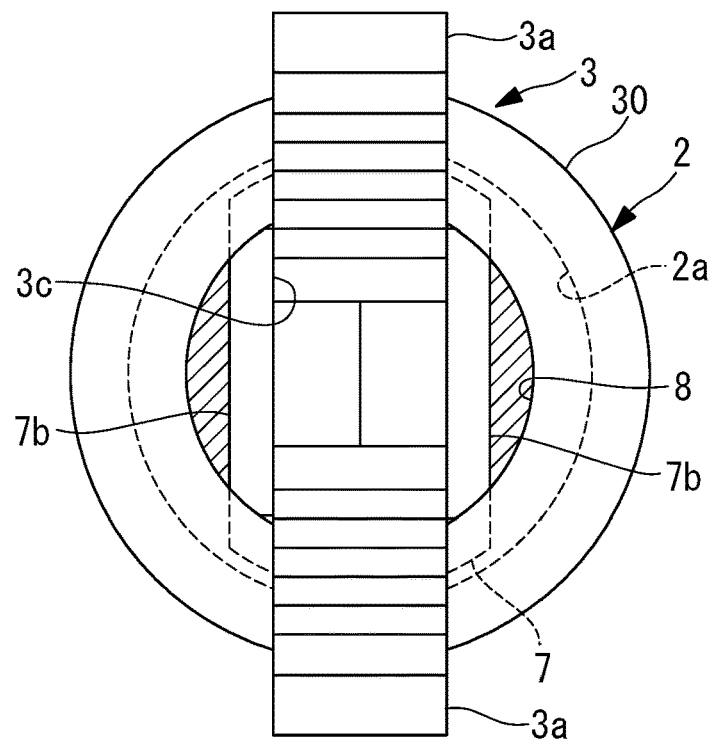
FIG. 7 is a front view of the endoscopic surgical device in FIG. 3.

In the example shown in FIG. 5, the recesses 7*b* have a shape obtained by cutting out the outer peripheral surface of the flow-path formation member 7 along two flat planes parallel to the axis of the center hole 7*a*. Moreover, as shown in FIGS. 6 and 7, the recesses 7*b* are disposed at positions opposite from each other with the bracket 3*c* interposed therebetween in a direction orthogonal to the opening-closing direction of the pair of forceps components 3*a* supported by the bracket 3*c*. Consequently, gaps between the inner peripheral surface of the distal end cover 30 and the recesses 7*b* constitute second liquid delivery holes 8 (hatched areas in FIGS. 6 to 8) through which the liquid guided through the sheath 2 is delivered in the forward direction.

Figure 9:
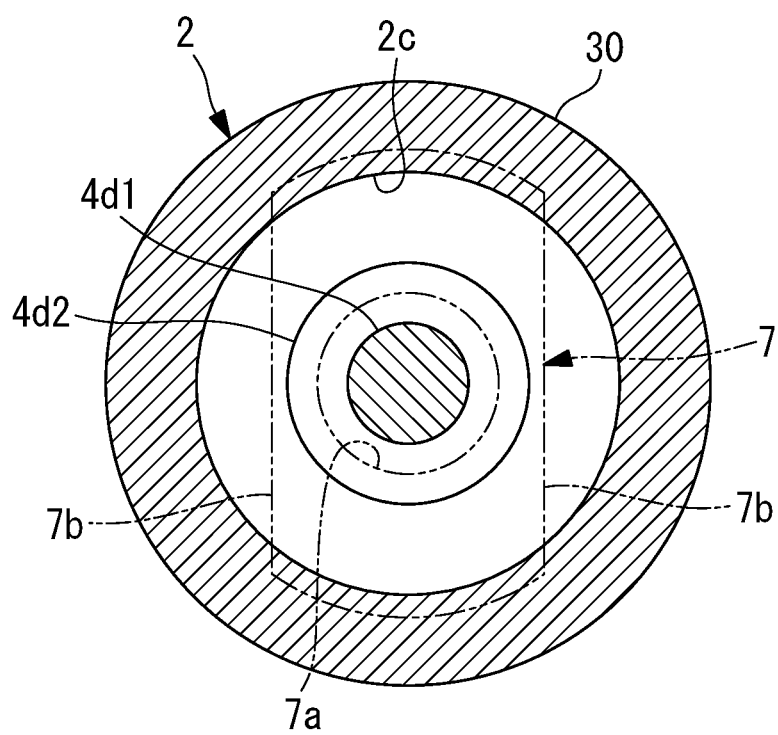
FIG. 9 is a cross-sectional view illustrating the relationship among a stopper section, the flow-path formation member, and an operable member provided within the sheath of the endoscopic surgical device in FIG. 1.

As shown in FIG. 9, the stopper section 2*c* has a periphery that is smaller than the maximum diameter of the flow-path formation member 7, and protrudes to a radial position larger than the recesses 7*b*.

The flow-path formation member 7 has a thickness slightly smaller than the distance between the collar section 2*b* and the stopper section 2*c*, and is disposed at a position interposed between the collar section 2*b* and the stopper section 2*c*. Thus, the flow-path formation member 7 is rotatable about a central axis of the sheath 2.

Figure 4:
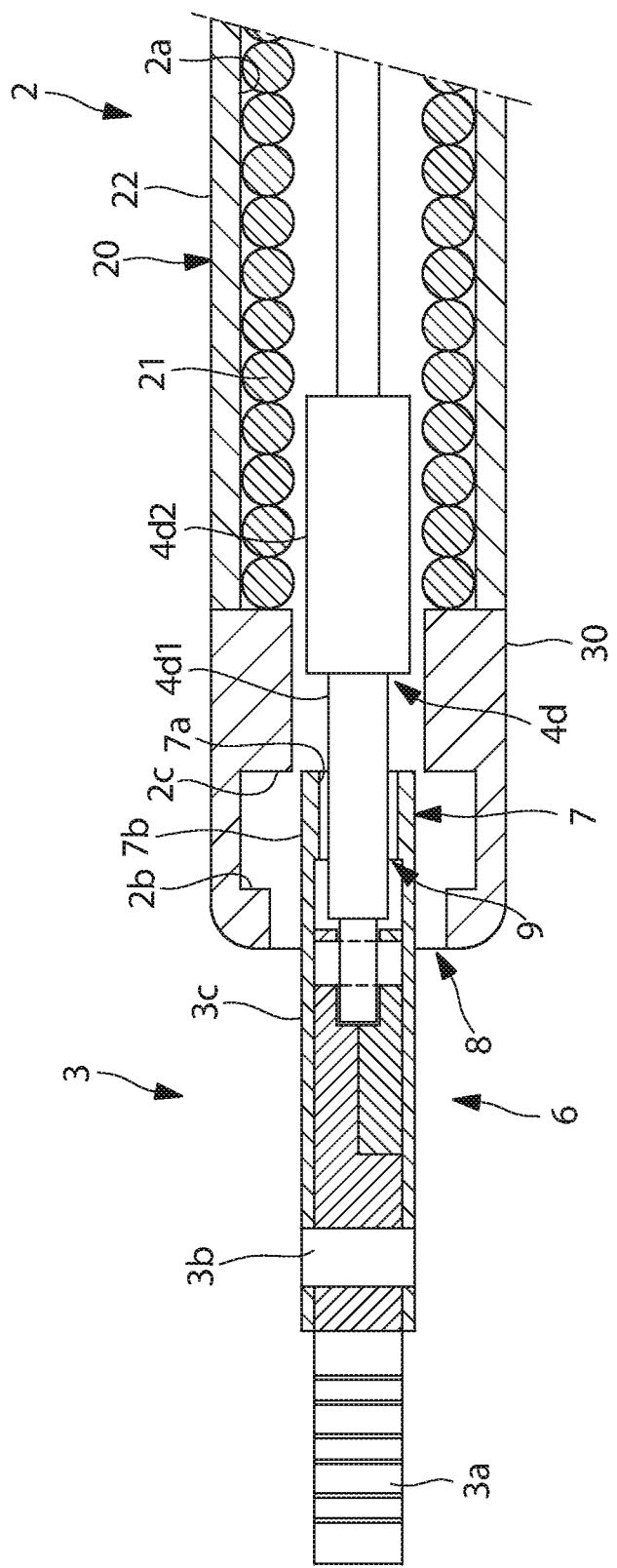
FIG. 4 is an enlarged vertical sectional view taken in a direction orthogonal to an opening-closing direction of the forceps components of the endoscopic surgical device in FIG. 1.

As shown in FIGS. 2 to 4, the operable member 4*d* includes a small-diameter section 4*d*1 extendable through the center hole 7*a* of the flow-path formation member 7 and a large-diameter section 4*d*2 disposed toward the proximal end relative to the small-diameter section 4*d*1 and having an outer diameter larger than the center hole 7*a*. Consequently, a gap between the small-diameter section 4*d*1 of the operable member 4*d* and the center hole 7*a* constitute a first liquid delivery hole 9. Then, when the operable member 4*d* is moved forward, the large-diameter section 4*d*2 of the operable member 4*d* abuts on the proximal end surface of the flow-path formation member 7 so as to block the first liquid delivery hole 9, as shown in FIG. 3. On the other hand, when the operable member 4*d* is moved rearward, as shown in FIGS. 2 and 4, the large-diameter section 4*d*2 moves away from the proximal end surface of the flow-path formation member 7 so as to open the first liquid delivery hole 9.

In this embodiment, the operable member 4*d*, the flow-path formation member 7, the link mechanism 6, the forceps components 3*a*, the coil sheath 21, the distal end cover 30, the bracket 3*c*, and the flow-path formation member 7 are composed of an electrically conductive material through which a high-frequency current can flow.

The operable section 4 includes a handle 4*b* having a hook hole 4*a* to be attached to the proximal end of the sheath 2 and a movable section 4*c* that is movable in the longitudinal direction of the sheath 2 relative to the handle 4*b*. Reference sign 4*e* denotes a hook hole provided in the movable section 4*c*.

When the movable section 4*c* is moved toward the distal end relative to the handle 4*b*, a pressing force is transmitted to the link mechanism 6 via the operable member 4*d* and causes the link mechanism 6 to operate, whereby the forceps components 3*a* are opened. When the movable section 4*c* is moved toward the proximal end relative to the handle 4*b*, a pulling force is transmitted to the link mechanism 6 via the operable member 4*d* and causes the link mechanism 6 to operate, whereby the forceps components 3*a* are closed.

A power source (not shown) is connected to the proximal end of the wire 4*f*, such that a high-frequency current can be applied to the forceps components 3*a* via the operable member 4*d*.

The handle 4*b* is provided with a connection port 10 that communicates with the flow path 2*a* of the sheath 2.

The liquid delivery means 5 is, for example, a syringe or a pump connected to the connection port 10. By activating the liquid delivery means 5, a liquid, such as a physiological saline solution, can be delivered to the flow path 2*a* of the sheath 2.

Next, the operation of the endoscopic surgical device 1 according to this embodiment having the above-described configuration will be described.

In order to perform endoscopic submucosal dissection by using the endoscopic surgical device 1 according to this embodiment, the forceps components 3*a* are closed by operating the operable section 4, as shown in FIG. 2. In this state, the sheath 2 is inserted into the body, starting from the distal end, via the channel in the insertion section of the endoscope until the distal end of the sheath 2 protrudes from the distal end of the insertion section of the endoscope.

Thus, the forceps components 3*a* disposed at the distal end of the sheath 2 are within the field of view of the endoscope, so that an operator performs treatment while checking an image acquired by the endoscope on a monitor. By applying a high-frequency current via the operable member 4*d* in the state where the forceps components 3*a* are closed, the forceps components 3*a* can be used as a high-frequency knife.

The procedure of the endoscopic submucosal dissection using the endoscopic surgical device 1 according to this embodiment is as follows.

First, a submucosal layer of a site considered to be a lesion to be excised in the endoscopic image displayed on the monitor is pierced with the forceps components 3*a* in the closed state, and a liquid, such as a physiological saline solution, is injected by means of the liquid delivery means 5, thereby causing the lesion site to bulge.

In this case, since the forceps components 3*a* are closed, the large-diameter section 4*d*2 of the operable member 4*d* is not blocking the first liquid delivery hole 9, as shown in FIGS. 2 and 4. Thus, the liquid guided to the distal end through the flow path 2*a* of the coil sheath 21 is delivered in the forward direction through both the first liquid delivery hole 9 and the second liquid delivery holes 8. Accordingly, the cross-sectional area of the flow path 2*a* can be increased, so that a large amount of liquid can be delivered. If a liquid with high viscosity, such as hyaluronic acid, is to be used as the liquid for causing the lesion site to bulge, the above configuration is advantageous in that a large cross-sectional area of the flow path 2*a* is ensured so that the liquid can be readily delivered.

Subsequently, by using the forceps components 3*a* in the closed state as a high-frequency knife, an initial dissection process is performed for forming holes at a plurality of locations spaced apart in the circumferential direction in a part of the mucous membrane around the lesion site.

Then, the forceps components 3*a* in the closed state are inserted into each of the holes formed in the initial dissection process. While a high-frequency current is applied to the forceps components 3*a* via the operable member 4*d*, the forceps components a are moved in a predetermined dissecting direction intersecting the longitudinal axis, so that the mucous membrane around the lesion site can be excised.

If bleeding occurs during the excision of the mucous membrane around the lesion site, the liquid delivery means 5 is activated so that the liquid is supplied into the flow path 2*a* of the coil sheath 21 and is used to wash away the blood and to clearly identify the bleeding site, thereby facilitating treatment for stopping the bleeding.

When performing treatment such as excising the dissected mucous membrane, the operator moves the movable section 4*c* toward the distal end relative to the handle 4*b* of the operable section 4, so that a pressing force is applied to the link mechanism 6 via the operable member 4*d*, thereby causing the pair of forceps components 3*a* to pivot in the opening direction. Then, by applying a twisting force to the operable member 4*d*, the flow-path formation member 7, the bracket 3*c*, and the forceps components 3*a* are rotated about the central axis of the sheath 2 relative to the sheath 2, so that the opening-closing direction of the forceps components 3*a* can be adjusted.

In this case, since the forceps components 3*a* are rotated about the central axis of the sheath 2 in a state where the forceps components 3*a* are supported by the sheath 2, the rotating motion of the forceps components 3*a* is supported by the sheath 2, and the opening-closing direction can be stably changed without significantly changing the position of the forceps components 3*a*, as compared with a case where the entire sheath 2 is rotated.

When the forceps components 3*a* are disposed in the opening-closing direction in which the mucous membrane can be readily gripped, the movable section 4*c* is moved toward the proximal end relative to the handle 4*b*, so that a pulling force is applied to the link mechanism 6 via the operable member 4*d*, thereby causing the pair of forceps components 3*a* to pivot in the closing direction. Consequently, treatment such as excising the mucous membrane by gripping it between the pair of forceps components 3*a* can be performed.

In this case, when the mucous membrane is to be gripped by the forceps components 3*a*, if the mucous membrane is covered with a liquid, such as blood, it is sometimes not possible to confirm the gripping position by using the endoscope. Thus, it is necessary to clean the mucous membrane in this treatment. Therefore, by activating the liquid delivery means 5, a liquid, such as a physiological saline solution, is delivered via the flow path 2*a* of the coil sheath 21.

As shown in FIG. 3, in a state where the forceps components 3*a* are open, the operable member 4*d* is moved forward so that the first liquid delivery hole 9 is blocked by the large-diameter section 4*d*2. Thus, the liquid is delivered in the forward direction via the second liquid delivery holes 8 alone. By reducing the cross-sectional area of the flow path 2*a*, the delivery rate of the liquid can be increased.

Because the second liquid delivery holes 8 are constituted by the gaps between the recesses 7*b* of the flow-path formation member 7 and the inner surface of the distal end cover 30, and the recesses 7*b* are disposed at positions opposite from each other with the bracket 3*c* interposed therebetween in the direction orthogonal to the opening-closing direction of the forceps components 3*a*, the liquid delivered from the second liquid delivery holes 8 is delivered straight in the forward direction without being hindered by the forceps components 3*a* in the open state. Consequently, the liquid at the target site can be washed away more reliably.

Figure 8:
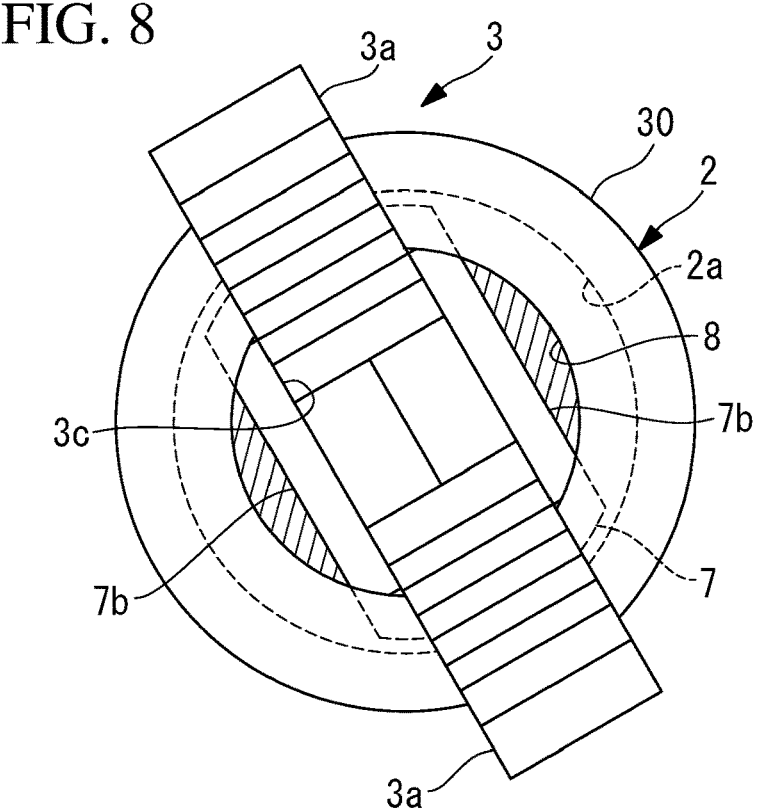
FIG. 8 is a front view illustrating a state where a forceps section of the endoscopic surgical device in FIG. 6 is rotated about a central axis of a sheath.

Because the flow-path formation member 7 is fixed to the bracket 3*c*, the recesses 7*b* are always disposed at the positions opposite from each other with the bracket 3*c* interposed therebetween in the direction orthogonal to the opening-closing direction of the forceps components 3*a*. This is advantageous in that, even if the opening-closing direction of the forceps components 3*a* is changed, the liquid to be delivered from the second liquid delivery holes 8 can be delivered straight in the forward direction, as shown in FIG. 8.

Consequently, the liquid can be delivered to wash the mucous membrane while the forceps components 3*a* are maintained in a standby state in which they are open for gripping the mucous membrane, and the confirmed mucous membrane can be immediately gripped by using the forceps components 3*a*.

According to this embodiment, the width of the forceps components 3*a* in the opening-closing direction thereof and the width of the forceps components 3*a* in the direction orthogonal to the opening-closing direction are both smaller than the width of the bracket 3*c*. Therefore, when the forceps components 3*a* are closed, the forceps components 3*a* are not in the way of the liquid delivered from the second liquid delivery holes 8, and the current density of the high-frequency current to be applied can be increased at the position of the forceps components 3*a*. This is advantageous in that the efficiency of dissection can be improved when the forceps components 3*a* are used as a high-frequency knife.

In the endoscopic surgical device 1 according to this embodiment, the forceps components 3*a* can be used as a high-frequency knife and as gripping forceps, and can also be used for washing or local injection by delivering a liquid in the forward direction whether the forceps components 3*a* are in either the closed state or the open state. Therefore, in the above-described endoscopic submucosal dissection, it is not necessary to insert and remove a plurality of surgical devices into and from the channel of the endoscope. This is advantageous in that treatment can be performed from the beginning to the end while the endoscopic surgical device 1 according to this embodiment is maintained in the inserted state.

In this embodiment, the second liquid delivery holes 8 are provided at the opposite sides of the bracket 3*c* in the direction orthogonal to the opening-closing direction of the forceps components 3*a*. Alternatively, only one of the sides may be provided with a second liquid delivery hole 8.

Furthermore, the shape of the recesses 7*b* constituting the second liquid delivery holes 8 is not limited to the shape obtained by cutting out the outer peripheral surface of the disk-shaped flow-path formation member 7 along flat planes, and may alternatively be another freely-chosen shape.

As a result, the above-described embodiment leads to the following aspect.

An aspect of the present invention provides an endoscopic surgical device including: a sheath insertable into a channel of an endoscope and having a pipe for delivering a liquid; a forceps section that is disposed so as to protrude from a distal end cover provided at a distal end of the sheath and that includes a pair of openable-closable forceps components; an operable member that is connected to a proximal end of the forceps section, opens the forceps components when the operable member is moved forward in a longitudinal direction thereof and closes the forceps components when the operable member is moved rearward; and a flow-path formation member that has a through-hole through which the operable member extends, the flow-path formation member including a first liquid delivery hole constituted by a gap between the through-hole and the operable member and a second liquid delivery hole constituted by a gap between the flow-path formation member and an inner peripheral surface of the distal end cover. The operable member is provided with a large-diameter section that abuts on the flow-path formation member when the operable member is moved forward so as to block the first liquid delivery hole.

According to this aspect, in a state where the sheath is inserted into the channel of the endoscope and the forceps section protruding from the distal end cover provided at the distal end of the sheath protrudes from the distal end of the endoscope, the operable member is operated at the proximal end of the sheath, so that the pair of forceps components of the forceps section can be opened and closed, whereby a target site can be treated. When the forceps components are opened by moving the operable member forward within the sheath, the large-diameter section provided in the operable member blocks the first liquid delivery hole, so that the liquid flowing through the sheath is delivered in the forward direction only from the second liquid delivery hole between the distal end cover and the flow-path formation member. Specifically, when the forceps components are opened, the flow area is reduced so that the liquid can be delivered at a high flow rate, whereby body fluid, such as blood, can be washed away efficiently.

On the other hand, when the forceps components are closed by moving the operable member rearward within the sheath, the large-diameter section provided in the operable member opens the first liquid delivery hole, so that the liquid flowing through the sheath is delivered through both the first liquid delivery hole and the second liquid delivery hole. Specifically, when the forceps components are closed, the flow area is increased, so that the liquid can be delivered by a large amount. Moreover, when performing local injection to a lower layer of the mucous membrane, the liquid can be readily delivered even if the viscosity thereof is high.

In the above aspect, the forceps section may include a bracket that supports the forceps components in an openable-closable manner, and the bracket may be fixed to the flow-path formation member.

Accordingly, by moving the operable member forward or rearward in the longitudinal direction of the sheath relative to the bracket fixed to the flow-path formation member, the pair of forceps components can be readily pivoted.

In the above aspect, the operable member may be disposed along a central axis of the sheath. The flow-path formation member may be rotatable relative to the sheath about a longitudinal axis of the sheath and may have a recess on at least one side in a direction orthogonal to an opening-closing direction of the forceps components. The recess is recessed radially inward and constitutes the second liquid delivery hole.

Accordingly, by rotating the bracket about the longitudinal axis of the sheath, the pivot plane of the pair of forceps components can be rotated about the longitudinal axis of the sheath. Thus, the direction in which the target site is to be gripped can be readily adjusted. In this case, the flow-path formation member fixed to the bracket also rotates about the longitudinal axis of the sheath simultaneously with the bracket, so that the position of the second liquid delivery hole relative to the forceps components does not change. In particular, the second liquid delivery hole is constituted by the gap between the recess provided on at least one side in the direction orthogonal to the opening-closing direction of the forceps components and the inner surface of the sheath, so that the liquid can be delivered in the forward direction without being hindered by the openable-closable forceps components.

In the above aspect, the recess of the flow-path formation member may include recesses at opposite sides of the through-hole.

Accordingly, the liquid can be delivered in a well-balanced manner from opposite sides of the forceps section.

In the above aspect, the forceps components and the operable member may each be composed of an electrically conductive material that allows a high-frequency current to flow therethrough.

Accordingly, with the high-frequency current applied via the operable member, the forceps section can be used as a high-frequency knife. Treatment that involves gripping with the forceps section, washing or local injection by delivering the liquid, or treatment that involves cutting with a high-frequency knife can be performed in a switchable manner in a state where the endoscopic surgical device is left inserted in the channel of the endoscope.

In the above aspect, the forceps section may include a bracket that supports the forceps components in an openable-closable manner; and, in a state in which the forceps components are closed, a width of the forceps components in an opening-closing direction may be smaller than that of the bracket.

In the above aspect, the forceps section may include a bracket that supports the forceps components in an openable-closable manner; and a width of the forceps components in a direction orthogonal to an opening-closing direction may be smaller than that of the bracket.

Accordingly, the density of the high-frequency current in the forceps section can be increased, thereby facilitating a cutting process.

The present invention is advantageous in that the liquid delivery mode can be switched in accordance with whether forceps are open or closed.

REFERENCE SIGNS LIST 1 endoscopic surgical device
2 sheath
2a flow path (pipe)
3 forceps section
3a forceps components
3c bracket
4d operable member
4d2 large-diameter section 7 flow-path formation member
7a center hole (through-hole)
7b recess
8 second liquid delivery hole
9 first liquid delivery hole
30 distal end cover

The invention claimed is:

1. An endoscopic surgical device comprising:
   a sheath insertable into a channel of an endoscope and having a flow path for delivering a liquid;
   a forceps section that is disposed so as to protrude from a distal end cover provided at a distal end of the sheath and that includes a pair of openable-closable forceps components;
   an operable member that is connected to a proximal end of the forceps section, and is configured to open the forceps components when the operable member is moved forward in a longitudinal direction thereof and close the forceps components when the operable member is moved rearward; and
   a flow-path formation member that has a through-hole through which the operable member extends, the flow-path formation member including:
      a first liquid delivery hole constituted by a gap between: (i) an inner surface of the flow-path formation member forming the through-hole and (ii) the operable member, and
      a second liquid delivery hole constituted by a gap between the flow-path formation member and an inner peripheral surface of the distal end cover,
   wherein:
      the operable member is provided with a large-diameter section that is configured to abut on the flow-path formation member when the operable member is moved forward so as to block the first liquid delivery hole,
      when the operable member is moved forward to open the forceps components, the large-diameter section is configured to abut on the flow-path formation member so as to block the first liquid delivery hole such that liquid flowing through the sheath is delivered forward in the longitudinal direction only through the second liquid delivery hole, and
      when the operable member is moved rearward to close the forceps components, the large-diameter section is configured to open the first liquid delivery hole such that the liquid flowing through the sheath is delivered forward in the longitudinal direction through both the first liquid delivery hole and the second liquid delivery hole.

2. The endoscopic surgical device according to claim 1, wherein:
   the forceps section includes a bracket that supports the forceps components in an openable-closable manner, and
   the bracket is fixed to the flow-path formation member.

3. The endoscopic surgical device according to claim 2, wherein:
   the operable member is disposed along a central axis of the sheath, and
   the flow-path formation member is rotatable relative to the sheath about a longitudinal axis of the sheath and has a recess on at least one side in a direction orthogonal to an opening-closing direction of the forceps components, the recess being recessed radially inward and constituting the second liquid delivery hole.

4. The endoscopic surgical device according to claim 3, wherein the recess of the flow-path formation member includes recesses at opposite sides of the through-hole.

5. The endoscopic surgical device according to claim 1, wherein the forceps components and the operable member are each composed of an electrically conductive material that allows a high-frequency current to flow therethrough.

6. The endoscopic surgical device according to claim 1, wherein:
   the forceps section includes a bracket that supports the forceps components in an openable-closable manner, and
   in a state in which the forceps components are closed, a width of the forceps components in an opening-closing direction of the forceps components is smaller than a width of the bracket.

7. The endoscopic surgical device according to claim 1, wherein:
   the forceps section includes a bracket that supports the forceps components in an openable-closable manner, and
   a width of the forceps components in a direction orthogonal to an opening-closing direction of the forceps components is smaller than that of the bracket.

8. The endoscopic surgical device according to claim 1, wherein:
   at least a part of the operable member is disposed away from an inner wall of the sheath to form a liquid delivery path in the sheath through which the liquid can be delivered;
   at least a part of the inner surface of the flow-path formation member is disposed away from the operable member; and
   the first liquid delivery hole and the second liquid delivery hole are each branched from the liquid delivery path.

9. The endoscopic surgical device according to claim 8, wherein the liquid delivery path, the first liquid delivery hole, and the second liquid delivery hole each extend in the longitudinal direction, and the device is configured to deliver liquid in the longitudinal direction through the liquid delivery path, the first liquid delivery hole, and the second liquid delivery hole.

10. The endoscopic surgical device according to claim 1, wherein the flow-path formation member is movable in the longitudinal direction with respect to the sheath.

11. The endoscopic surgical device according to claim 1, wherein the device is configured to deliver the liquid forward in the longitudinal direction through the second liquid delivery hole to outside of the distal end cover at a position on a radially outer side of the forceps components.

* * * * *